(12) United States Patent
Bestgen et al.

(10) Patent No.: US 8,738,632 B2
(45) Date of Patent: May 27, 2014

(54) ENCODED MATRIX INDEX

(75) Inventors: Robert J. Bestgen, Rochester, MN (US); Thomas J. Eggebraaten, Rochester, MN (US); Jeffrey W. Tenner, Rochester, MN (US)

(73) Assignee: International Business Machines Corporation, Armonk, NY (US)

( * ) Notice: Subject to any disclaimer, the term of this patent is extended or adjusted under 35 U.S.C. 154(b) by 28 days.

(21) Appl. No.: 13/422,560

(22) Filed: Mar. 16, 2012

(65) Prior Publication Data

US 2012/0179712 A1    Jul. 12, 2012

Related U.S. Application Data

(62) Division of application No. 12/140,816, filed on Jun. 17, 2008.

(51) Int. Cl.
    *G06F 17/30*    (2006.01)
(52) U.S. Cl.
    USPC .......................................... 707/744; 707/690
(58) Field of Classification Search
    USPC .................................................. 707/690, 744
    See application file for complete search history.

(56) References Cited

U.S. PATENT DOCUMENTS

| | | | | |
|---|---|---|---|---|
| 5,706,495 A | * | 1/1998 | Chadha et al. | 707/2 |
| 5,930,785 A | * | 7/1999 | Lohman et al. | 707/2 |
| 6,725,223 B2 | * | 4/2004 | Abdo et al. | 707/100 |
| 6,745,211 B2 | * | 6/2004 | Kabasakalian et al. | 707/690 |
| 2003/0233353 A1 | * | 12/2003 | Taylor | 707/3 |
| 2007/0198621 A1 | * | 8/2007 | Lumsdaine et al. | 708/200 |

OTHER PUBLICATIONS

U.S. Patent and Trademark Office, Office Action issued in related U.S. Appl. No. 12/140,816, dated Jun. 2, 2011.
U.S. Patent and Trademark Office, Office Action issued in related U.S. Appl. No. 12/140,816, dated Mar. 12, 2012.

* cited by examiner

*Primary Examiner* — Apu Mofiz
*Assistant Examiner* — Chelcie Daye
(74) *Attorney, Agent, or Firm* — Wood, Herron & Evans, LLP

(57) ABSTRACT

A method, apparatus, and program product are provided for creating an Encoded Matrix Index for a column in a database table. An element of the column for all rows in the database table is compared to a corresponding reference value in a reference data structure, and in response to at least one value for the element of the column not matching the reference value, indicating a variation in a variation data structure and creating a value data structure. Queries executed using the Encoded Matrix Index include terms associated with a sub-column defined in a column of a database table. The variation data structure is accessed to determine whether any variation exists between rows belonging to a sub-column of the database table. If no variation exists, a value is accessed from the reference data structure; otherwise, a value for each row of the sub-column is accessed from a value data structure.

15 Claims, 14 Drawing Sheets

ENCODED MATRIX INDEX

CROSS-REFERENCE TO RELATED APPLICATIONS

This application is a divisional of U.S. patent application Ser. No. 12/140,816, filed on Jun. 17, 2008 by Robert J. Bestgen et al., the entire disclosure of which is incorporated by reference herein.

FIELD OF THE INVENTION

The present invention relates to computers and data processing, and more particularly to indices utilized for database queries.

BACKGROUND OF THE INVENTION

Relational databases are being considered for storing sequence data that has the characteristics of long repeating sequences generally consisting of a relatively small number of distinct values. However, there are currently no acceptable solutions to efficiently query such sequences. Because of this, the sequence data is generally not being stored relationally or only small portions of the sequence data is being stored. The lack of relational sequence data and the storage of only small portions of the sequence data make it difficult to mine the data. An example of such sequence data is genomic sequence data.

Genomic sequence data is typically represented as long sequences of letters or numbers each having a small number of distinct values. Storage and query of genomic sequence data is problematic in a relational database because of its size. The entire human genome consists of approximately 3 billion base pairs. Base pairs are two nucleotides on opposite complementary DNA or RNA strands connected via a hydrogen bond. Each nucleotide is typically represented by the letters A, C, G, and T, which correspond to the long names adenine, cytosine, guanine, and thymine. Sequences are represented by combining the letters of the nucleotides. For example, a small sequence may be represented by AGAATTCA.

Variations in DNA sequences of humans can affect how a human develops a disease or reacts to treatment. A single variation in a nucleotide within a DNA fragment is called a Single Nucleotide Polymorphism or SNP. For example, one individual may have a DNA fragment of AGAATTCA and another individual may have a similar DNA fragment of AGAATCCA. In such a case, the two possible sequences are called alleles and are typically named after the variation such as a T allele for the first individual and a C allele for the second individual. There are an estimated 5-10 million SNPs in the human genome; however, only 0.1% of the DNA is different from one individual to another.

Humans are diploid organisms, which mean they have two copies of every chromosome. Therefore, in humans, there can be three possible combinations of alleles, for example CC, CT, and TT. The combination an individual has for a specific trait is called their genotype. Therefore, the possible genotypes with regard to the SNP in the above example would be CC, CT, or TT. A notation using 0, 1, and 2 is also used to represent an individual's genotype where 2 represents the case where the chromosomes contain different alleles (e.g. CT), 0 indicates the major (aka wild or common type) allele and 1 indicates the minor (aka mutation) allele.

An individual's genotype does not specifically identify which SNPs are on which chromosomes. The identification of which SNPs are on each chromosome is the haplotype of an individual. A 0/1 vector is generally used for the haplotype where a zero indicates the major allele and a one indicates the minor allele. Chip arrays have been developed that can detect the presence of SNPs in a DNA sample. Current chips support detection of up to 900,000 SNPs. Comparisons of retrieval and analysis of sequences, SNPs, genotype, and haplotype are all critical to understanding the genetic association of disease and treatment efficacy.

Genomic data is filled with large strings of characters, which have a small number of distinct values, presenting a challenge for storing the data in a relational database as well as mining the data stored. In a relational database, data is arranged into rows and columns, with each row generally corresponding to a record and each column generally corresponding to a field of data for each record. Some possible approaches to storing the sequence data include, storing the sequences for a patient a single column, using a column for each element of the sequence (e.g. nucleotide, SNP), or using a row for each element of the sequence for each patient.

A problem with the first approach is that the data is seen as a large string to the database, which introduces inefficiencies when trying to quickly identify specific variations within a sequence. Some databases have the ability to define arrays to the database; however, the individual elements cannot be indexed. The second and third approaches enable the database system to easily navigate the data; however, the second approach generates more columns than contemporary relational database systems can typically support and the third approach results in inefficient processing of the table due to the large number of rows. Moreover, Bioinformatics and computational biology, which involve the use of techniques including applied mathematics, informatics, statistics, computer science, artificial intelligence, chemistry, and biochemistry to solve biological problems usually on the molecular level, typically generate data as sequences and breaking the sequences apart into columns or rows is not consistent with efficient data generation.

What is needed, therefore, is an efficient index design for a column that can be used by database queries to more efficiently search sequence type data stored in relational databases.

SUMMARY OF THE INVENTION

Embodiments of the invention provide a method, apparatus and program product that utilize an Encoded Matrix Index data structure that may be used by database queries to address deficiencies in searching sequence type data stored in relational databases. An Encoded Matrix Index is based in part on the premise of storing reference values for portions of sequence data that often represent the most common values found in a particular type of sequence data in a column of a database table, and storing additional information regarding the variation of specific sequences relative to those reference values. By storing only portions of sequences in the column that vary from the reference values, the amount of information necessary to represent the sequences in the index may be greatly reduced as compared to storing the sequences themselves. Additionally, the sequences can be easily reconstructed based upon the reference values and the variations therefrom when the sequence data or portions thereof are retrieved from the index.

In one embodiment of the invention, an Encoded Matrix Index may be generated for a column in a database table by comparing values for an element of the column for all rows in the database table to a corresponding reference value for the element in a reference data structure. If the value for the element of the column does not match the reference value for the element, a variation is indicated for the element of the column in a variation data structure, and a value data structure is created representing values for the element of the column for all rows in the database table. The element may include an array having a plurality of values for each row in the database table, or the element may include a single value for each row in the database table. In some embodiments, the variation data structure may be a binary structure having a bit for each element of the column, where each bit within the structure indicates a variation for a corresponding element, though other structures may be utilized in other embodiments. Some embodiments further include mapping the element to a bitmap representation using a map structure, where the value data structure stores the bitmap representation of the value for each row. For these embodiments the map structure generally includes a plurality of distinct values and a plurality of bitmap values corresponding to each of the plurality of distinct values, where each bitmap value is incremented based on the preceding bitmap value.

In an alternate embodiment for generating the Encoded Matrix Index for a column in a database table, a reference data structure is generated including a reference value for each sub-column defined within the column. A variation data structure indicates, for all rows in the database table, whether any variation exists between the sub-column and the reference data structure. For each sub-column in which variation in any row exists, a value data structure is generated representing a value for each row of the sub-column. The sub-column for some embodiments includes a portion of the column at each row of the plurality of rows. The sub-column may contain a single sub-unit, or the sub-column may contain a plurality of sub-units. In some embodiments, for each row among the plurality of rows, the sub-column is mapped to a bitmap representation using a map structure. The value data structure for these embodiments stores the bitmap representation of the value for each row. In these embodiments the map structure generally includes a plurality of distinct values and a plurality of bitmap values corresponding to each of the plurality of distinct values, where each bitmap value is incremented based on the preceding bitmap value.

Embodiments of the invention may execute a database query using the Encoded Matrix Index. In response to a database query that includes a term associated with a sub-column defined in a column of a database table, a variation data structure is accessed from the Encoded Matrix Index to determine whether any variation exists between rows belonging to the sub-column of the database table. If no variation exists, a value is accessed from the reference data structure from the Encoded Matrix Index, which is associated with the sub-column, and a determination whether the value from the reference data structure matches the term in the data base query. If a variation does exist, the value data structure from the Encoded Matrix Index is accessed and a value is identified for each row of the sub-column to determine which elements of the sub-column, if any, match the term in the database query. In some embodiments the value data structure includes a bitmap mapping of the value for each row of the sub-column.

Other embodiments of the invention maintain an Encoded Matrix Index corresponding to a column in a database table. In these embodiments, a variation data structure is updated to reflect a change to the database table. The updated variation data structure is checked for each sub-column defined with the column. If there is no variation in the updated variation data structure, then for all rows among a plurality of rows, if any new variation exists as a result of the update between the sub-column and the reference data structure the variation data structure is updated to indicate the variation. Additionally, for each sub-column in which variation exists in any row, a value data structure is generated representing a value for each row of the sub-column. In some embodiments, the reference data structure may also be updated to reflect updates to reference values for each of the plurality of rows of a sub-column defined within the column.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the principles of the invention.

DETAILED DESCRIPTION

Figure 1:
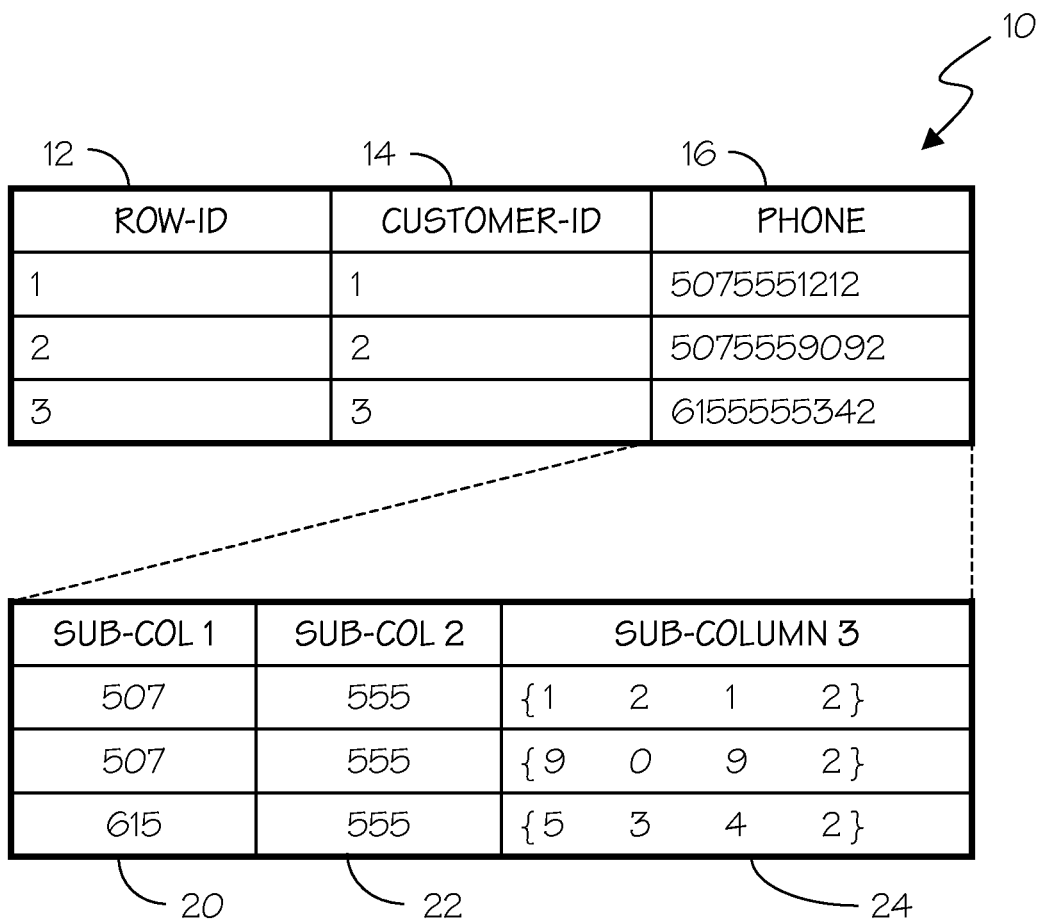
FIG. 1 shows an exemplary table containing sequence data with one possible representation of the sequence data divided into sub-columns.

Embodiments of the invention generate and use an Encoded Matrix Index to address deficiencies in the art related to searching sequence type data stored in relational databases. An Encoded Matrix Index typically relies at least in part on reference values that store portions of sequence data that often represent the most commonly occurring values found in a particular type of sequence data in a column of a database table, combined with additional information that specifies the variation of specific sequences relative to those reference values.

Additional details regarding Encoded Matrix Indices will discussed in greater detail below; however, before discussing these additional details, a brief explanation of various other types of indices is provided by way of background. Query optimizers may create temporary objects or index objects as part of the optimization process to assist with complex and nested queries. These temporary objects may be optimized subsets of the overall optimization including partially optimized tables, or specially created indexes. For example, the query optimizer may analyze a row selection in a query and use that analysis to determine if creation of a separate object containing an index may be beneficial. These objects are generally temporary in nature, meaning that they may persist until the system is restarted, until the underlying data has changed, or until the object is no longer needed. Index objects are more often of a permanent nature (across system restarts). Both temporary objects and temporary index objects are generally stored in query plan caches which allow for the use and reuse of the temporary objects in an effort to save time and processing for subsequent queries.

Indices are one way of providing quicker access to data. Indices can be created on any combination of attributes on a relation. Queries that filter using those attributes can find matching tuples randomly using the index, without having to check each tuple in turn. Relational databases typically supply multiple indexing techniques, each of which is optimal for some combination of data distribution, relation size, and typical access pattern. B+ trees, R-trees, and bitmaps. A B+ tree is a type of tree which represents sorted data in a way that allows for efficient insertion, retrieval and removal of records, each of which is identified by a key. R-trees are tree data structures that are similar to B-trees, but are used for spatial access methods i.e., for indexing multi-dimensional information; for example, the (X, Y) coordinates of geographical data. Bitmaps are a special kind of index that work well for data such as gender, which has a small number of distinct values, e.g., Male and Female, but many occurrences of those values, which would happen if, for example, you had gender data for each resident in a city. Bitmap indexes have a significant space and performance advantage over other structures for such data. Bitmap indexes use bit arrays (commonly called "bitmaps") and answer queries by performing bitwise logical operations on these bitmaps. Indices are usually not considered part of the database, as they are considered an implementation detail, though indices are usually maintained by the same group that maintains the other parts of the database.

One such index object is an encoded vector index ("EVI"). An EVI is a data structure that is made up of two primary components: a symbol table and a vector. The symbol table contains the distinct key values in the rows covered, as well as statistical information about each key. The statistical information typically includes a numeric 'gray' code identifying the key, the first and last rows where the key is found, and the number of times the key appears in the table. The vector corresponds to the actual rows in the table and contains a list of byte codes indicating which key each row contains. EVIs are a complementary alternative to existing index objects, such as binary radix tree structure-logical files or SQL indices, and are a variation on bitmap indexing. EVIs are usually recommended for larger tables with a low number of distinct values for the index key. Because of their compact size and relative simplicity, EVIs provide for faster scans of a table that may also be processed in parallel. A database engine may use the vector portion of the EVI to build a dynamic bitmap that contains one bit for each row in the table. If the row satisfies a query selection, the bit is set on. If the row does not satisfy the query selection, the bit is set off. Similar to a bitmap index, intermediate dynamic bitmaps can be AND'ed and OR'ed together to satisfy an ad hoc query.

As noted above, embodiments of the invention may be used in connection with storing and accessing sequence type data in a database table. To address concerns such as using a relational table to store sequence data in the form of large strings where a significant portion of the strings contains overlapping sequence data, or storing sequence data across multiple columns or multiple rows, each having a portion of the sequence data, which is incompatible with the way that the information is viewed and/or used, it is desirable to store sequence data for a particular record within a single column, with portions of the sequence data arranged into sub-columns defined within a particular column. However, it has been found that EVIs are poorly suited for use with sequence type data stored in a column, as EVIs are generally unable to map distinct values within a sub-column of a column, which can be helpful for sequence type data stored in a table where there may be very many unique values for a particular column, but there may still be very few unique values within a sub-column. EVIs generally can only deal with a small number of unique values for a column. Therefore, to address the shortcomings of EVIs with respect to sequence type data, the illustrated embodiments utilize a different type of index, referred to herein as an Encoded Matrix Index (EMI), to better accommodate sequence data having many unique values for a particular column, but having relatively few unique values within a sub-column.

An Encoded Matrix Index (EMI) is a data structure that includes at least a reference data structure, a variation data structure and value data structure. The reference data structure generally contains a reference value used to compare against contents of portions of a column in a database table. The variation data structure is used to indicate if there is a variation between the reference value in the reference data structure and any of the rows associated with the portions of the column. The value data structure is used to store values associated with each of the rows when there is a variation associated with a portion of the column, as indicated in the variation data structure. In the illustrated embodiments, for example, the EMI includes the following items. A control data structure is defined in the EMI associating an application table's column with associated sub-columns, sub-units, variation vector, and reference data structures. The sub-column data structure is an application-defined portion of a column used for querying data. For example, the sub-column is a subset of the column that slices across all rows of data. To define the column as a structure, several sub-columns may be defined for the same column and each sub-column may be of a different length. Sub-columns may also be defined as an array, which implies that all elements of the array are the same size and have the same set of possible values. The sub-unit data structure may be defined in the case where a sub-column is an array. The sub-unit represents an element of this array. If the sub-column is not an array, then the sub-unit is the same as the sub-column. The variation vector data structure is a bit string with each bit representing the state of a sub-unit of a column with regard to the variation across the rows of data. For example, if the bit is on ("1"), the sub-unit does not have the same value across all rows. If the bit is off ("0"), all the rows are the same value for the sub-unit. The reference data structure is a string representing a reference to compare for variations across rows. In some embodiments, the reference data structure may be determined based on the first non-null insert of data, though in other embodiments, other methods may be used to determine the content of the reference data structure.

The data structure for the sub-columns may also store information for each sub-column. Generally, there is one sub column data structure per EMI control structure. In the illustrated embodiments, the sub-columns structure includes each sub-column's external name, its position within the original data, its length in bytes, the length of an element if the sub-column is an array, the length of a bitmap in a maps data structure, the position of the first sub-unit within the sub-units data structure, and a pointer to the maps data structure for the sub column. The maps data structure is a structure, which stores the mapping of the possible values for a sub-unit to, for example, an internal bitmap representation, though other representations may also be used. The number of bits required to store the values may be determined based on the number of possible values of the sub-unit.

The data structure for the sub-units may also store information for each sub-unit. Generally, there is one sub-unit data structure per EMI control structure. The sub-units data structure may additionally include a byte offset of the sub-unit relative to the column start, a length of the sub-unit, and a pointer to a value vector data structure for the sub-unit, if the subunit has a corresponding value vector. The value vector data structure contains an array of bitmaps where each bitmap specifies the mapped value, as defined in the maps data structure, of the sub-unit for a particular row. The size of the bitmap is the same as the size of the sub-unit identified by the sub-columns data structure.

To further clarify the data structures defined above, FIG. 1 illustrates a sample database table containing customer phone information for which an EMI can be generated. Referring now to FIG. 1, the table 10 is comprised of three columns, row-id 12, customer-id 14 and phone number 16. For this example, an EMI will be generated for the customer phone column 16. The phone number data is a form of sequence data that may have many similarities even though the value for each column may be different. For example, the phone number data can be broken down into area code, prefix, and the number as represented by three possible sub-columns 20, 22, 24. The third sub-column 24, may be broken down even further into individual digits of the number. An example of an SQL statement to create an EMI for the Phone column 16 might be:

```
CREATE ENCODED MATRIX INDEX ON SCHE-
   MA.CUSTDATA(PHONE) WITH SUBCOL-
   UMNS(AREACODE CHAR(3), PREFIX CHAR
   (3), NUMBER ARRAY(4) OF CHAR(1))
   CHECK(AREACODE IN ('507', '615', '702'),
   PREFIX IN ('555', '212', '284', '367'), NUM-
   BER IN ('0', '1', '2', '3', '4', '5', '6', '7', '8',
   '9')
``` where CUSTDATA is table 10 in FIG. 1.

Figure 2:
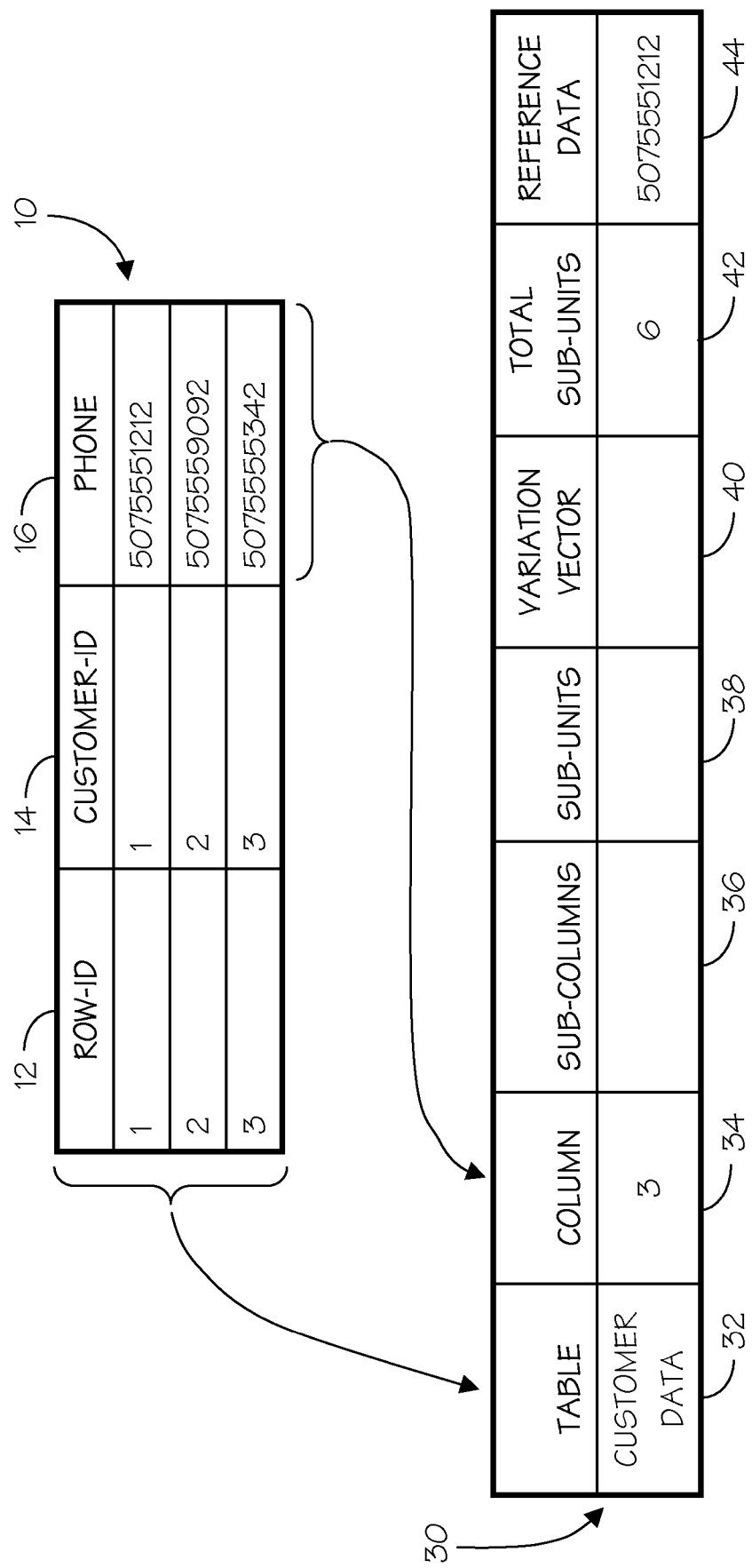
FIG. 2 shows an Encoded Matrix Index control data structure generated from the table in FIG. 1.

In one embodiment, the initial data structure created from this exemplary SQL command would be the EMI control data structure. Referring now to FIG. 2, one suitable implementation of an EMI control data structure 30 contains a reference 32 to the customer data table, a column indicator 34 identifying the column of the customer data table on which the EMI is being constructed, a pointer 36 to a sub-column data structure, a pointer 38 to a sub-units data structure, a pointer 40 to a variation vector data structure, the total sub-units 42 in the sub-unit data structure, and a reference data structure 44. In this example the value of the reference data structure 44 is the first non-null value in the phone column 16 in the customer data table 10. That value is "5075551212" and will be used for comparison with the other values in the phone column 16 when creating the remaining data structures for the EMI.

Figure 3:
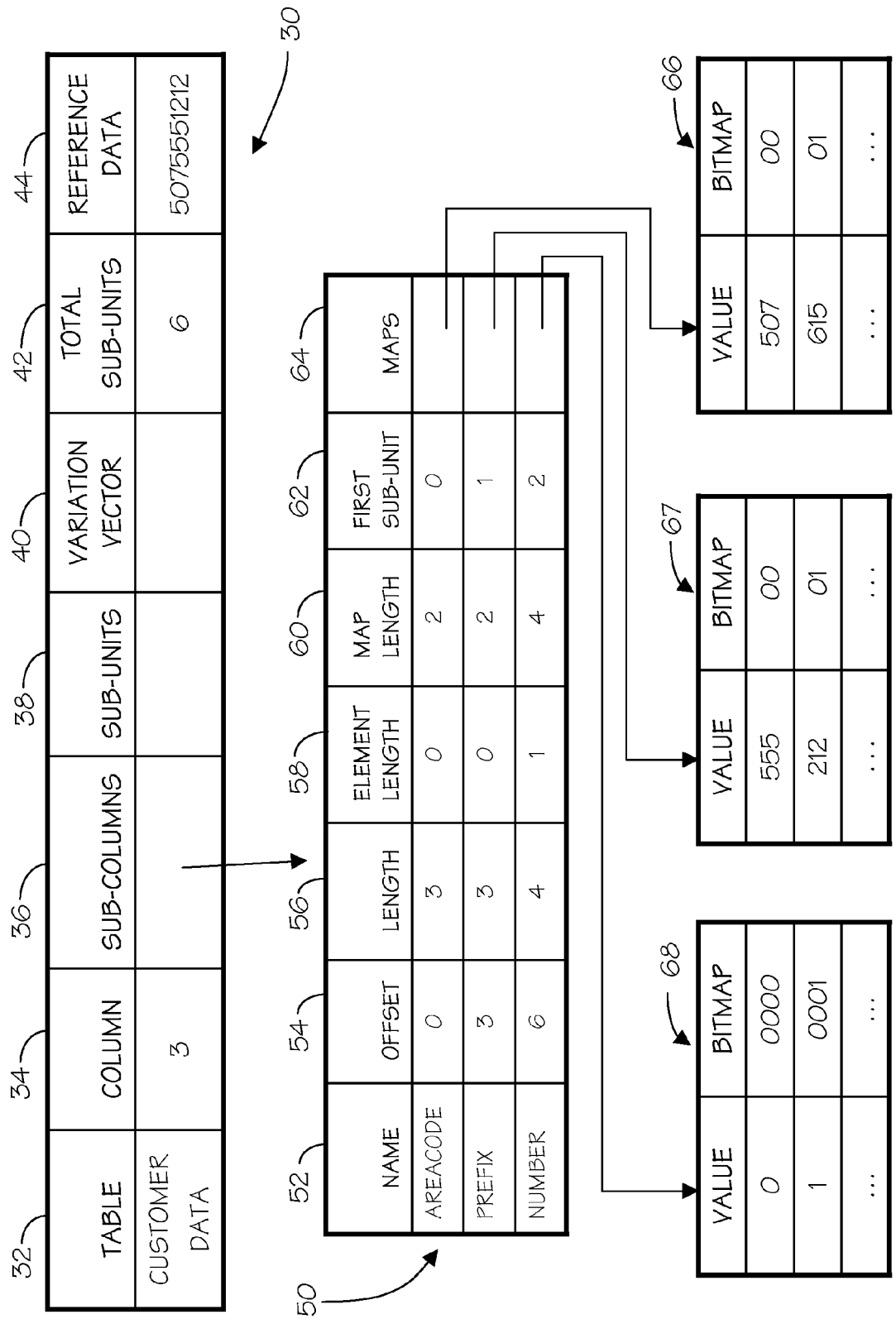
FIG. 3 shows a sub-column data structure and map data structures associated with the EMI control data structure of FIG. 2.
Figure 5:
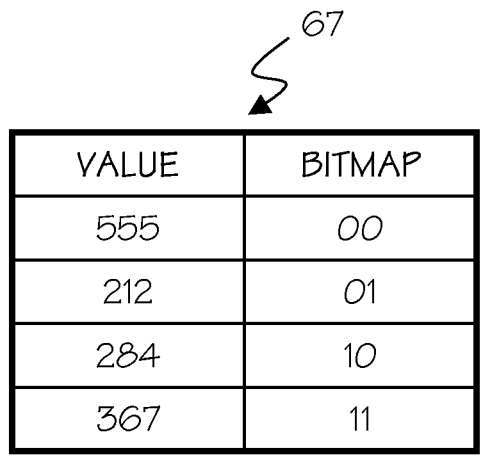
FIG. 5 shows a complete map data structure from FIG. 3.
Figure 6:
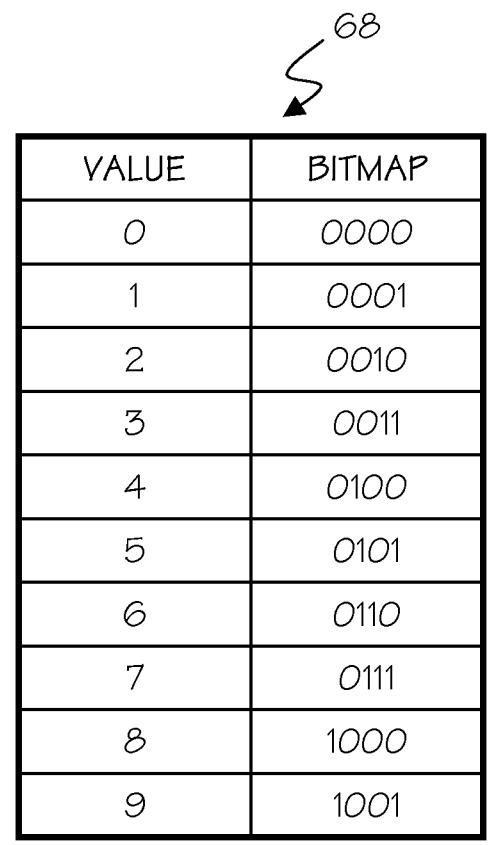
FIG. 6 shows a complete map data structure from FIG. 3.

One suitable implementation of a sub-column data structure 50, shown in FIG. 3, contains data related to the three sub-columns defined above. Elements of the sub-column data structure 50 include a name 52 of the sub-column (Area Code, Prefix, and Number for this example), an offset 54 representing the starting position of the column in the sub-column, the length 56 of the sub-column, an element length 56 of the sub-column, a map length 60 representing the length of a bitmap representing a value in some embodiments, a pointer 62 into a sub-units data structure indicating the starting point of the sub-column, and a pointer 64 to map data structures 66-68 for each of the sub-columns. Complete versions of the map data structures 66-68 may be seen in FIGS. 4-6 respectively. In the illustrated embodiment, the map data structures map possible sub-column/sub-unit values to bitmaps. In other embodiments, the map data structures may map the sub-column/sub-unit values to other values or data representations.

For example, for the prefix sub-column, the data in the sub-column data structure 50 would be as follows. The name 52 indicating the prefix, and specified by the exemplary SQL command above would be "PREFIX". The offset 54 value for the prefix would be "3" indicating that the first three characters are skipped and the prefix begins at the fourth character. The length 56 of the prefix is "3" because the prefix is represented by a three digit value. The element length 58 for the prefix would be "0" indicating that the prefix is a single value as opposed to an array of values. In contrast, the number sub-column is an array of single digit values, so its length would be "4" and its element length would be "1" indicating four single digit values. The map length of the prefix would be "2" because the values of the prefix can be represented by a 2-digit binary number, which can be seen in the table 67 in FIG. 5. Here there are four possible values for the sub-column, which can be represented by two binary digits.

Figure 7:
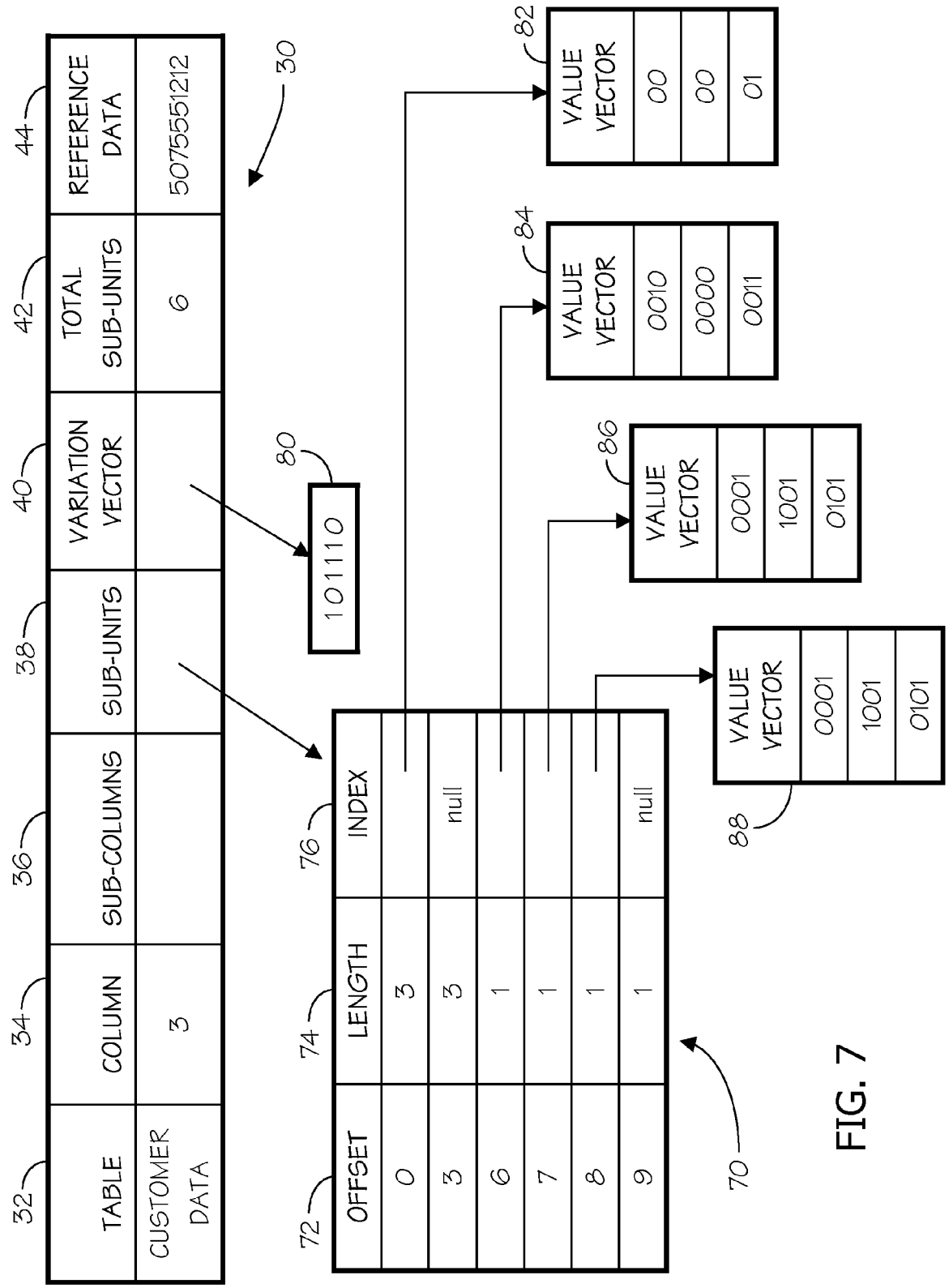
FIG. 7 shows a sub-unit data structure, a variation data structure and value vectors associated with the EMI control data structure of FIG. 2.

One suitable implementation of a sub-unit data structure 70, shown in FIG. 7, contains data related to the sub-units corresponding to the sub-columns defined in the sub-column data structure 50 (FIG. 3). The sub-unit data structure 70 contains an offset 72 value corresponding to the start position of the sub-column/sub-unit with the column 16 of the table 10 in FIG. 1. Associated with each sub-unit is a length 74 of the sub-unit and an index 76, which points to a value vector when there is a variation between the reference data structure 44 and the sub-unit. The variation is tracked in a variation vector data structure 80, which is associated with the pointer 40 in the EMI control data structure 30. The number of bits in the variation vector data structure 80 for the present embodiment corresponds to the number of sub-units in the sub-unit data structure 70, where a "0" indicates no variation between the sub-unit and the reference data structure 44 and a "1" indicates that there is a variation and that a value vector exists with bitmaps of the value. Put another way, a "0" for a sub-unit indicates that for every row in the table, that sub-unit contains the same value, and that value corresponds to the value for the sub-unit as represented in the reference data structure. A "1" for a sub-unit, on the other hand, indicates that at least one row in the table contains a value that differs from the value represented in the reference data structure, so the value vector will need to be accessed to determine the appropriate value for that sub-unit for any given row in the table.

Figure 4:
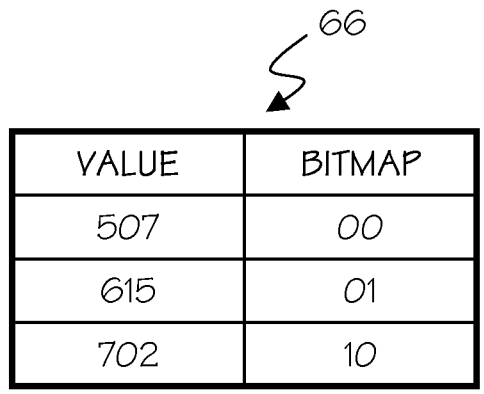
FIG. 4 shows a complete map data structure from FIG. 3.
Figure 8A:
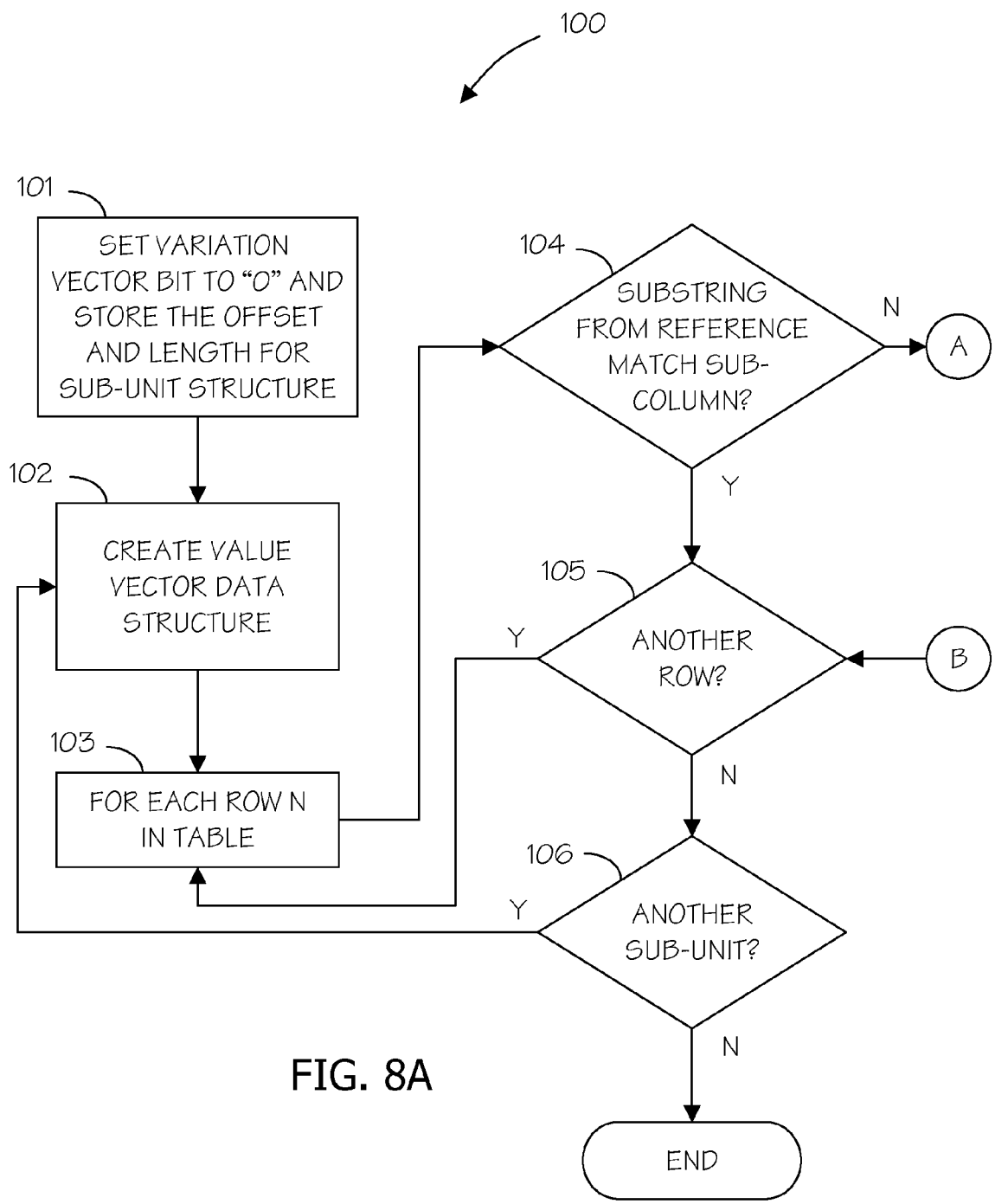
FIG. 8A is a flowchart illustrating a sequence of operations for creating an Encoded Matrix Index.
Figure 8B:
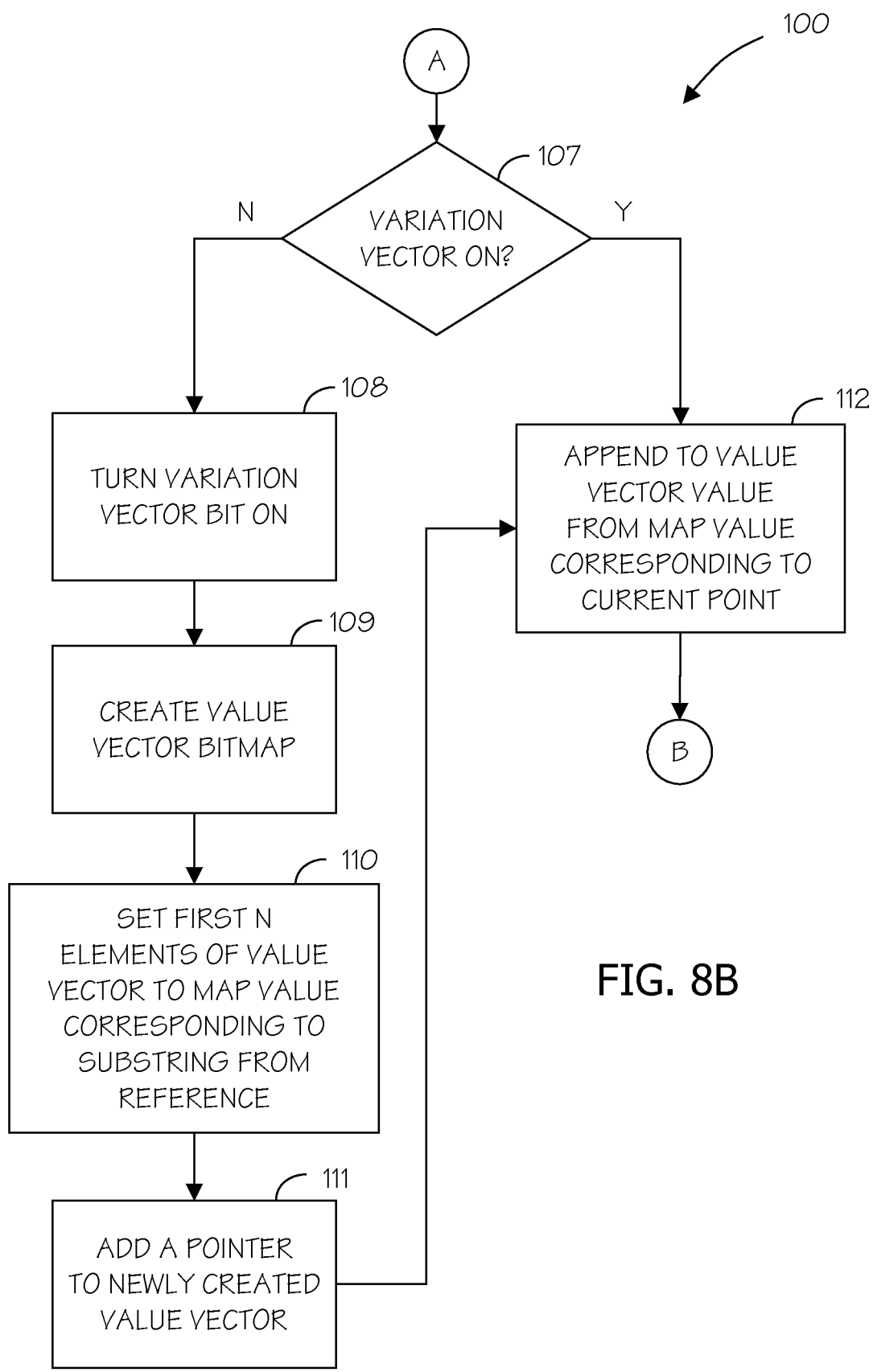
FIG. 8B is a continuation of the flowchart of FIG. 8A.

In the illustrated embodiment, there are six sub-units, one for the area code, one for the prefix, and four for the four-element array representing the number. In this embodiment and with additional reference to the flowchart 100 in FIG. 8A and FIG. 8B, when the sub-unit data structure 70 is initially created, the variation vector data structure 80 is also created (block 101). Additionally a value vector data structure is created (block 102). For the first row (block 103) in the sub-unit data structure 70, the offset of the value is zero and it has a length of three. The comparison value from the reference data structure with a zero offset and a length of three is "507". The first bit of the variation vector data structure 80 associated with the first sub-unit is initially set to "0" to indicate that it is not yet known that any row of the table includes a value for the area code unit that differs from the comparison value in the reference data structure. Each row for the sub-column is then checked against the value from the reference data structure (block 104). Proceeding through the data of the sub-column corresponding to the area code, row 1 of table 10 has an area code sub-column value of "507" so no variation is indicated ("Yes" branch of decision block 104). Proceeding with the next row ("Yes" branch of decision block 105), the second row also has an area code sub-column value of "507", also indicating no variation ("Yes" branch of decision block 104). Proceeding with the next row ("Yes" branch of decision block 105), however, the third row of the table has an area code value of "615", so upon reaching this row (associated with the "No" branch of decision block 104), a check is made to determine if the corresponding bit in the variation vector data structure is on. If the bit is off ("No" branch of decision block 107), the first bit in the variation vector data structure 80 is set to "1" (block 108) to indicate that at least one row of the table includes a value for the area code unit that differs from the comparison value in the reference data structure, and a corresponding value vector bitmap is created (block 109). The positions in the value vector preceding the current position are all filled with the corresponding bitmap from the reference data structure 44 (block 110). For example, the value "507" is mapped to bitmap "00", so the value vector 82 would contain bitmap "00" for the first and second rows. A pointer to the value vector 82 is stored in the index 76 (block 111). The third row of the value vector 82 would then contain the bitmap corresponding to the value of the sub-column "615", which is bitmap "01" (block 112). If the variation vector bit had already been on ("Yes" branch of decision block 107), then the bitmap representing the value in the current row would be appended to the value vector data structure 82 (block 112). The bitmap values are obtained from the map data structure 66 (FIG. 4).

Moving to the next sub-unit ("Yes" branch of decision block 106), which represents the second sub-column, the value starting at the fourth position (offset of three) and having a length of three from the reference data structure 44 is "555". The second bit of the value vector 80 corresponding to the second sub-unit is initially set to a zero. As seen in the phone data column 16 in table 10, all of the prefix values are "555" and the second bit of the value vector 80 remains a "0" indicating no variation ("Yes" branch of decision block 104). Here a null value may be stored in the index 76 for this sub-unit.

The remaining sub-units, corresponding to the individual digits of the number sub-column, are processed similar to the area code and prefix above, resulting in a variation vector data structure 80 having a value of "101110" indicating no variation for the second and sixth sub-unit, and indicting a variation and creation of corresponding value vectors 82-88 for the first, third, fourth and fifth sub-units. The process ends after all of the sub-units have been processed. The EMI for the phone column 16 of the table 10 in FIG. 1 thus includes the data structures illustrated in FIGS. 2-7 as described above.

Figure 9:
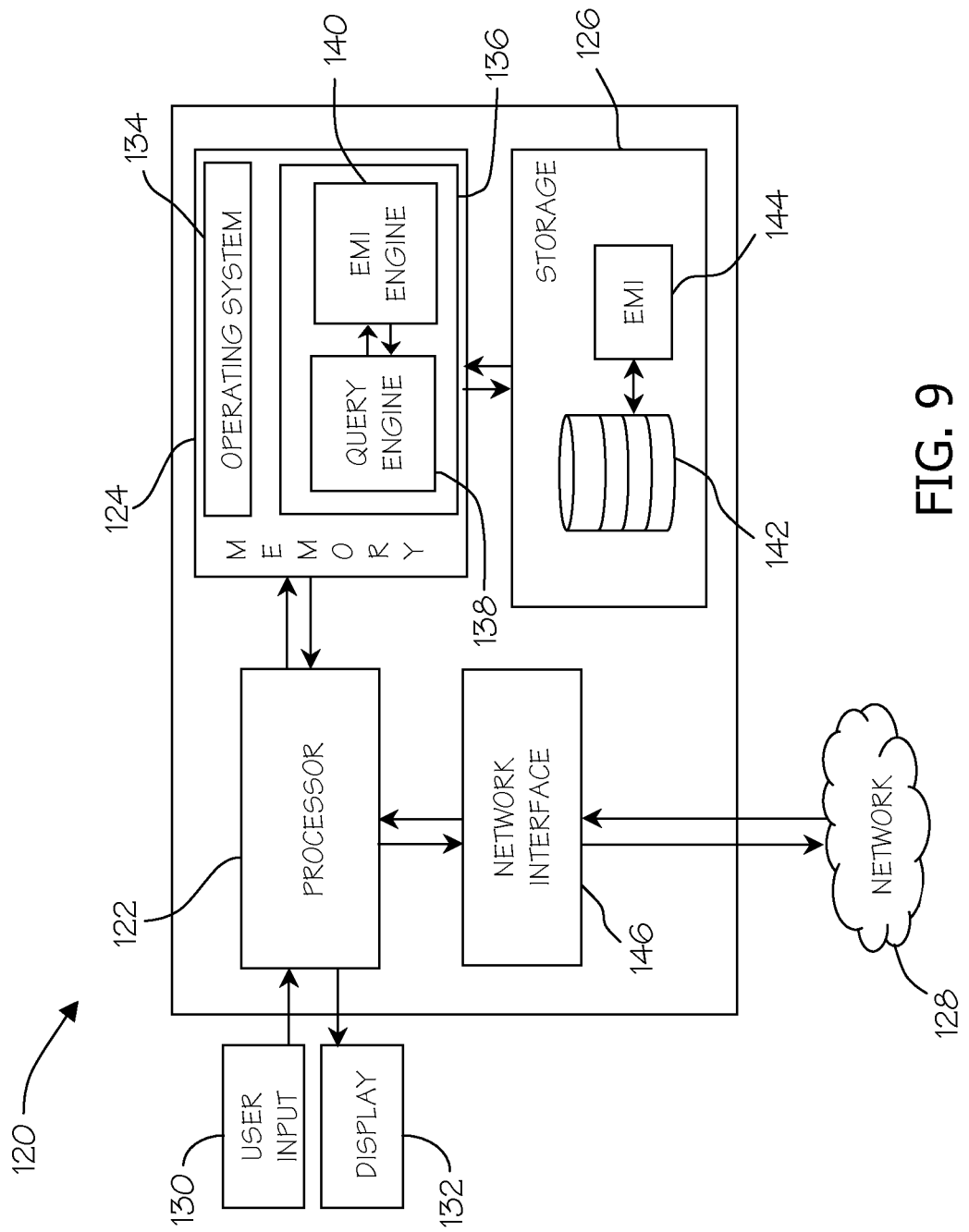
FIG. 9 is a block diagram of an exemplary hardware and software environment for a computer suitable for implementing the Encoded Matrix Index data structures consistent with embodiments of the invention.

Database queries and creation of index structures, as the EMI above, are generally implemented in a database management system executing in a compute environment such as an individual machine or a client-server environment. FIG. 9 illustrates an exemplary hardware and software environment for an apparatus 120 suitable for database management, execution of queries and creation of Encoded Matrix Index entities consistent with the invention. For the purposes of the invention, apparatus 120 may represent practically any computer, computer system, or programmable device e.g., multi-user or single-user computers, desktop computers, portable computers and devices, handheld devices, network devices, mobile phones, etc. Apparatus 120 will hereinafter be referred to as a "computer" although it should be appreciated that the term "apparatus" may also include other suitable programmable electronic devices.

Computer 120 typically includes at least one processor 122 coupled to a memory 124. Processor 122 may represent one or more processors (e.g. microprocessors), and memory 124 may represent the random access memory (RAM) devices comprising the main storage of computer 120, as well as any supplemental levels of memory, e.g., cache memories, non-volatile or backup memories (e.g. programmable or flash memories), read-only memories, etc. In addition, memory 124 may be considered to include memory storage physically located elsewhere in computer 120, e.g., any cache memory in a processor 122, as well as any storage capacity used as a virtual memory, e.g., as stored on a mass storage device 126 or another computer coupled to computer 120 via a network 128.

Computer 120 also typically receives a number of inputs and outputs for communicating information externally. For interface with a user or operator, computer 120 typically includes one or more user input devices 130 (e.g., a keyboard, a mouse, a trackball, a joystick, a touchpad, a keypad, a stylus, and/or a microphone, among others). Computer 120 may also include a display 132 (e.g., a CRT monitor, an LCD display panel, and/or a speaker, among others). The interface to computer 120 may also be through an external terminal connected directly or remotely to computer 120, or through another computer communicating with computer 120 via a network 128, modem, or other type of communications device.

Computer 120 operates under the control of an operating system 134, and executes or otherwise relies upon various computer software applications, components, programs, objects, modules, data structures, etc. (e.g. database application 136). Application 136, for example, may further include database queries 138 querying data base tables 142 and/or an EMI engine 140 generating EMI data structures 144. Computer 120 communicates on the network 128 through a network interface 146.

In general, the routines executed to implement the embodiments of the invention, whether implemented as part of an operating system or a specific application, component, program, object, module or sequence of instructions will be referred to herein as "computer program code", or simply "program code". The computer program code typically comprises one or more instructions that are resident at various times in various memory and storage devices in a computer, and that, when read and executed by one or more processors in a computer, causes that computer to perform the steps necessary to execute steps or elements embodying the various aspects of the invention. Moreover, while the invention has and hereinafter will be described in the context of fully functioning computers and computer systems, those skilled in the art will appreciate that the various embodiments of the invention are capable of being distributed as a program product in a variety of forms, and that the invention applies equally regardless of the particular type of computer readable media used to actually carry out the distribution. Examples of computer readable media include but are not limited to physical, recordable type media such as volatile and non-volatile memory devices, floppy and other removable disks, hard disk drives, optical disks (e.g., CD-ROM's, DVD's, etc.), among others, and transmission type media such as digital and analog communication links.

In addition, various program code described hereinafter may be identified based upon the application or software component within which it is implemented in specific embodiments of the invention. However, it should be appreciated that any particular program nomenclature that follows is merely for convenience, and thus the invention should not be limited to use solely in any specific application identified and/or implied by such nomenclature. Furthermore, given the typically endless number of manners in which computer programs may be organized into routines, procedures, methods, modules, objects, and the like, as well as the various manners in which program functionality may be allocated among various software layers that are resident within a typical computer (e.g., operating systems, libraries, APIs, applications, applets, etc.), it should be appreciated that the invention is not limited to the specific organization and allocation of program functionality described herein.

Those skilled in the art will recognize that the exemplary environment illustrated in FIG. 8 is not intended to limit the present invention. Indeed, those skilled in the art will recognize that other alternative hardware and/or software environments may be used without departing from the scope of the invention.

Figure 10A:
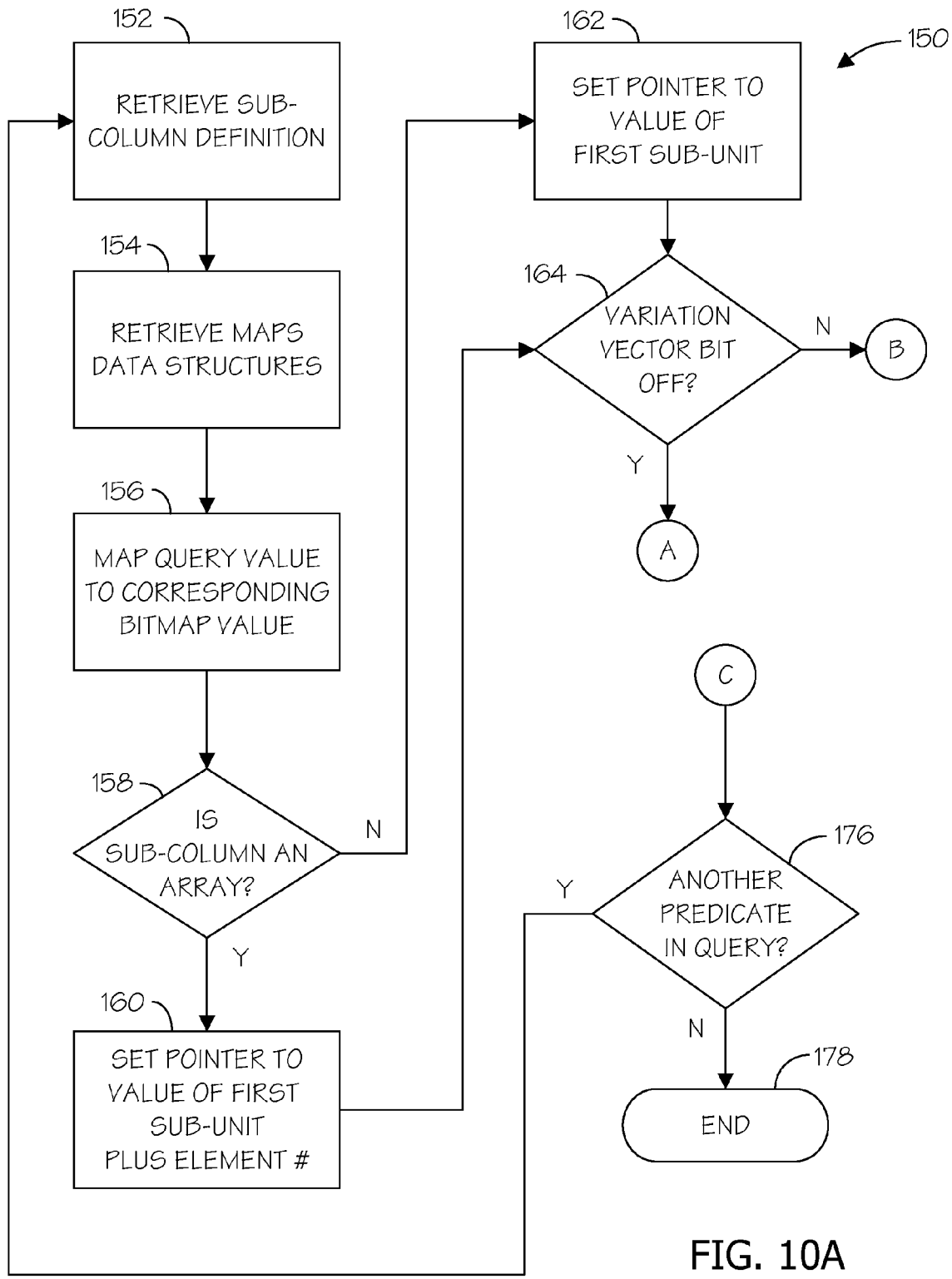
FIG. 10A is a flowchart illustrating a sequence of operations performed for a database query using an Encoded Matrix Index.
Figure 10B:
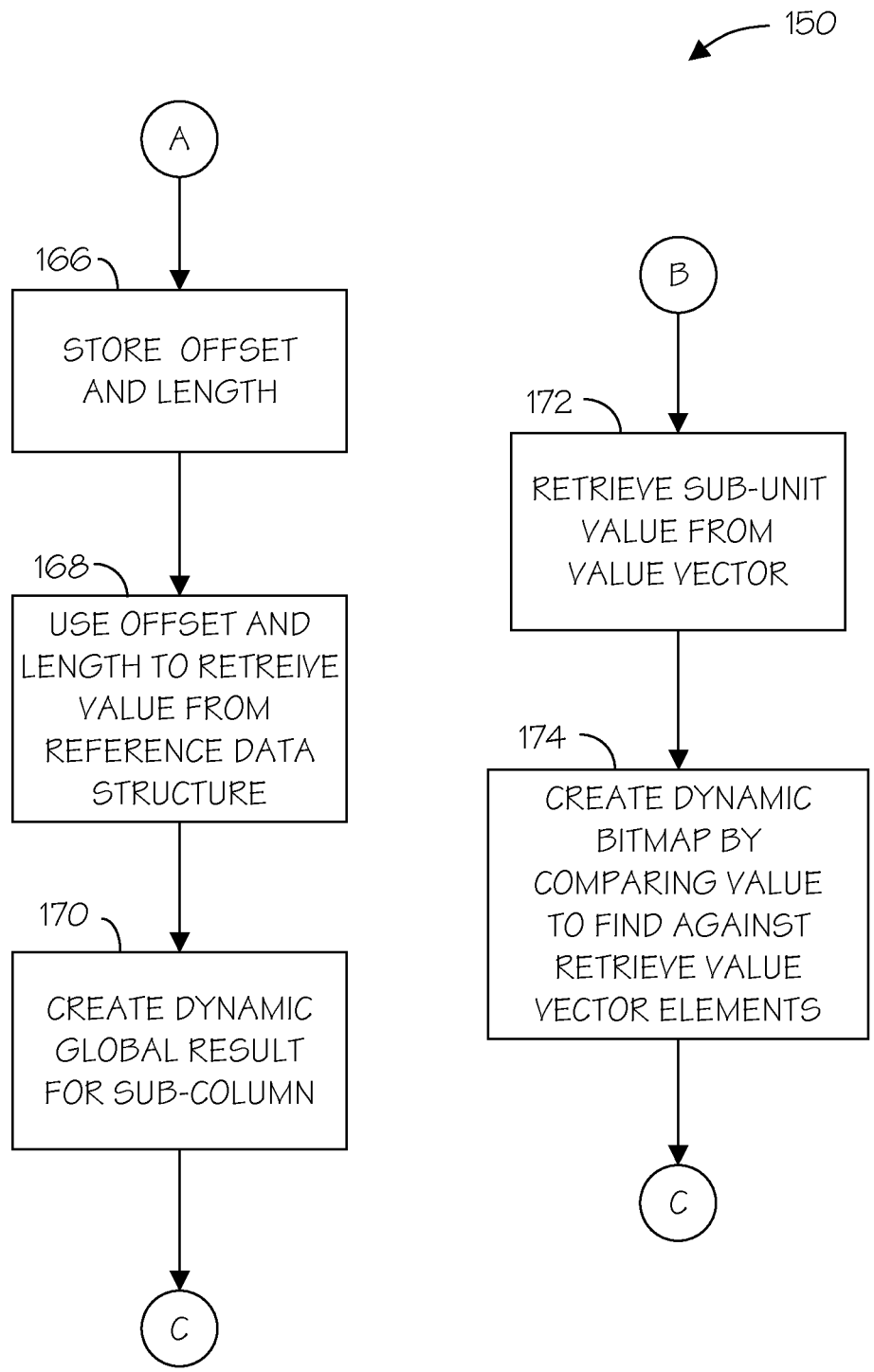
FIG. 10B is a continuation of the flowchart of FIG. 10A.

Once the Encoded Matrix Index has been created, it can be used to query the sequence data stored in the corresponding column of the data base table. FIG. 10A and FIG. 10B illustrate a flowchart 150 showing a method of using an EMI for a database query. After the query has been initiated, the EMI control data structure is referenced for sub-column definitions corresponding to the column being queried (block 152). The maps data structures are retrieved from the sub-column data structure (block 154) and the query value is mapped to a corresponding bitmap value (block 156) from the maps data structure corresponding to the sub-column associated with the query value.

If the sub-column associated with the query is an array ("Yes" branch of decision block 158), then the pointer within the sub-units data structure is set to the value of the first sub-unit of the sub-column plus the element number within the array (block 160). For example if the second sub-column is an array, and the third element of the array is the subject of the query, the pointer would be set to 1 (offset from sub-column data structure)+3 (third element in array), so that value would be found at the fourth position in the sub-units data structure. Otherwise, if the sub-column is not an array ("No" branch of decision block 158), the pointer is set based on the offset of the sub-column (block 162).

Once the position has been determined, the variation vector data structure is referenced check for a variation. If the corresponding bit in the variation vector is off ("Yes" branch of decision block 164), then the offset and the length of the sub-column are stored (block 166) and used to retrieve the value from the reference data structure (block 168). For example, if the offset for the sub-column is two and the length of the sub-column is four, then the value is retrieved from the second through fifth positions in the reference data structure. Because there is no variation for this sub-column among all of the rows, a global result can be created for this sub-column (block 170). If the bit in the variation vector data structure is on, indicating a variation ("No" branch of decision block 164), then the value vector is retrieved that corresponds to the sub-unit (block 172). A dynamic bitmap may then be created by comparing the query value against the retrieved value vector elements (block 174).

If there is another predicate in the query ("Yes" branch of decision block 176), then the process may be repeated starting at block 152. If there are no additional predicates ("No" branch of decision block 176) then the process ends (block 178) and the query engine may continue to perform the query using the results obtained from the EMI.

Figure 11:
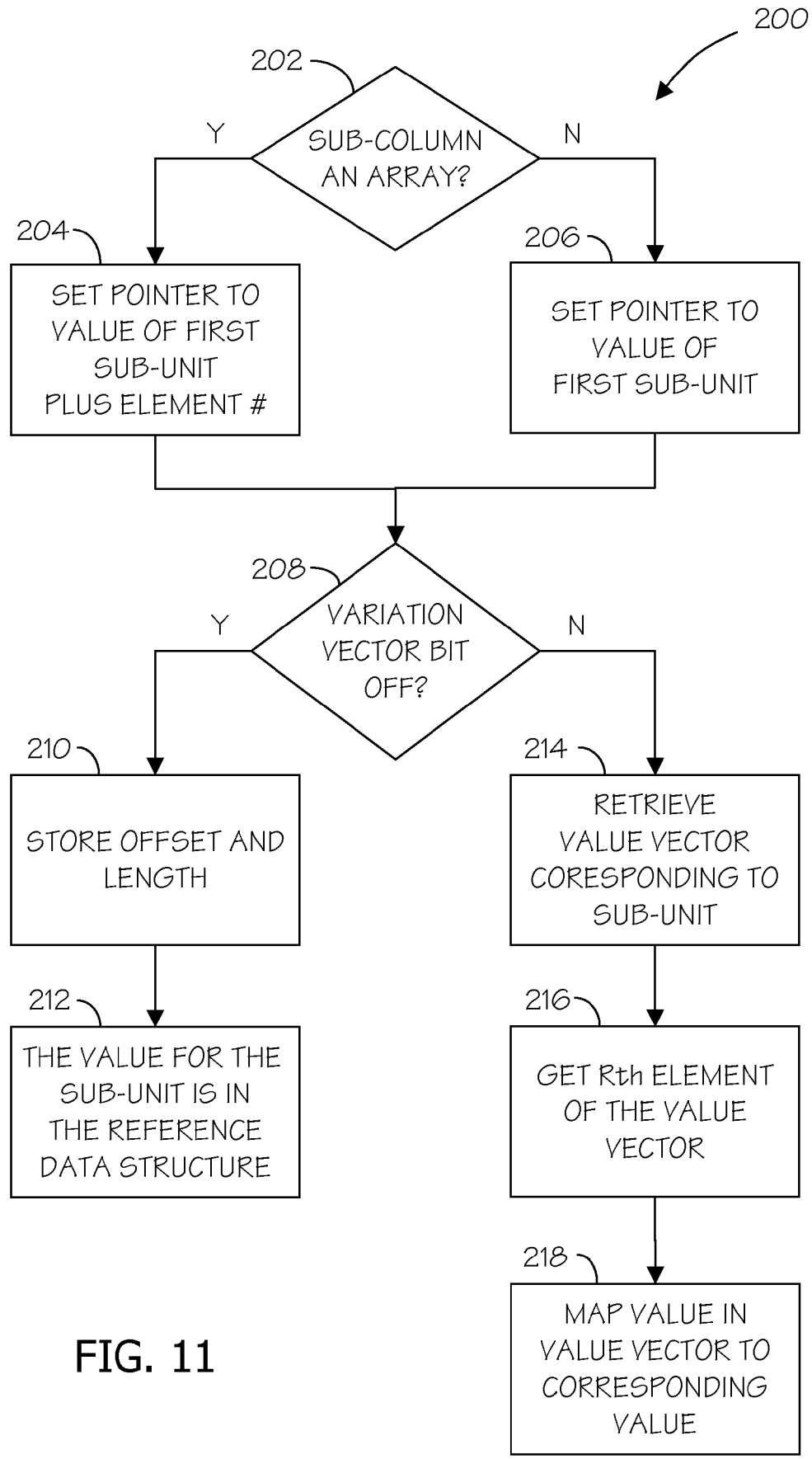
FIG. 11 is a flowchart illustrating a sequence of operations for retrieving values associated with the query in the flowchart in FIGS. 10A and 10B.

In the above query, no values from the "sequence" column were returned in the query results. If the query had asked that the values be returned, the EMI engine would use the result of the bitmap AND or OR processing to determine which rows satisfy the query, and then probe into the rows as seen in flowchart 200 in FIG. 11. If the sub-column associated with the query term is an array ("Yes" branch of decision block 202), the pointer into the sub-unit data structure is set similar to above by setting the pointer to the first sub-unit plus the element number within the sub-column array (block 204). If the sub-column is not an array ("No" branch of decision block 202), the pointer into the sub-unit data structure is set to the first sub-unit (block 206). If the bit in the variation vector corresponding to the pointer in the sub-unit data structure is off ("Yes" branch of decision block 208), the offset and length of the sub-unit is stored (block 210) and used to retrieve the value from the reference data structure (block 212). For example, as above, if the offset for the sub-column is one and the length of the sub-column is three, then the value is retrieved from the first through third positions in the reference data structure. This value is applicable to all rows for this sub-column. If the bit in the variation vector corresponding to the pointer in the sub-unit data structure is on ("No" branch of decision block 208), then assume that the row to be probed is held in a variable "R". The value vector corresponding to the current sub-unit in the sub-unit data structure is retrieved (block 214). The Rth element of the value vector corresponding to the Rth row is retrieved (block 216). The element retrieved from the value vector is converted from a bitmap representation back to a value by referencing the appropriate map data structure associated with the sub-column (block 218). This process may be repeated for each of the rows matching the query criteria.

Figure 12:
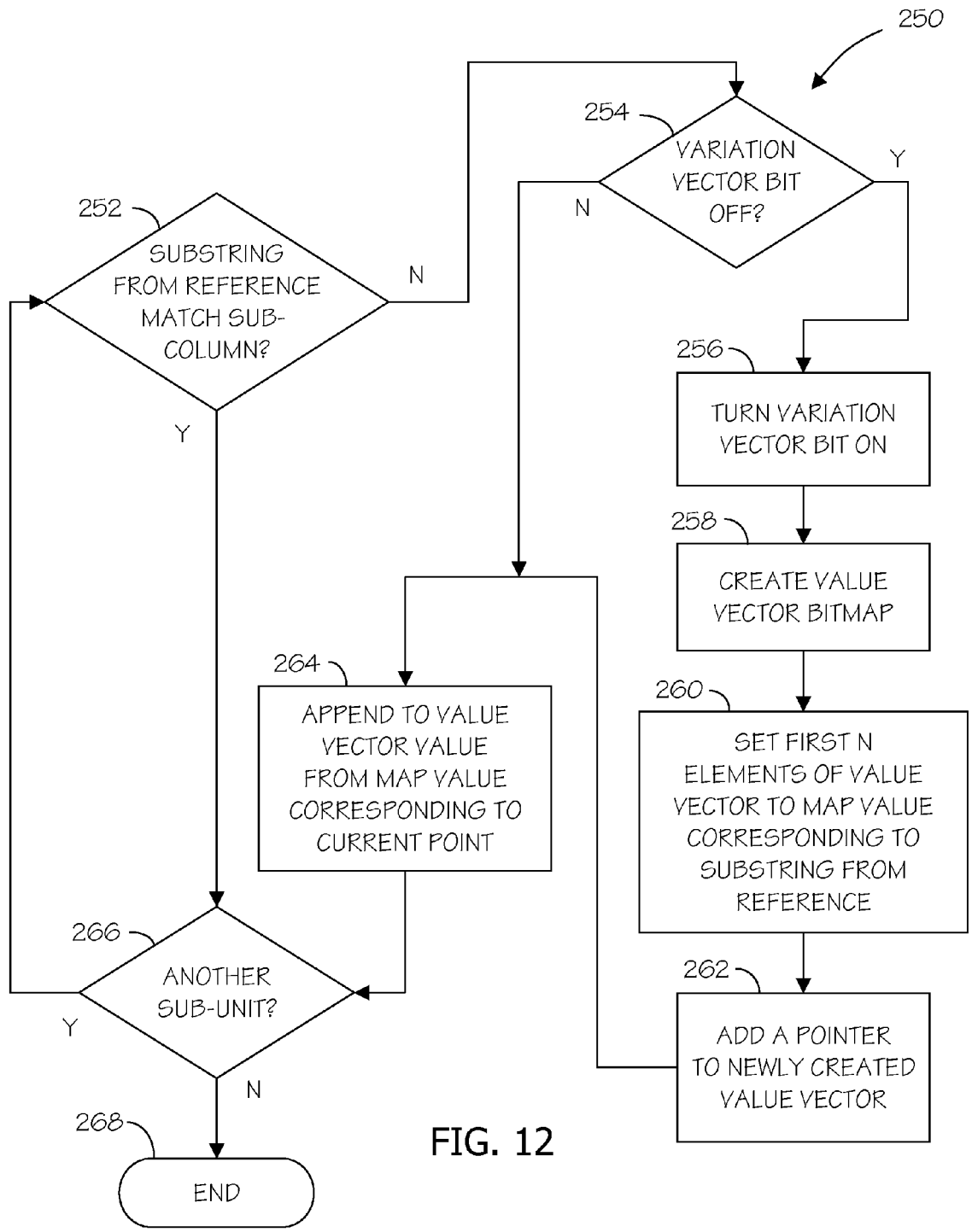
FIG. 12 is a flowchart illustrating a sequence of operations for updating an Encoded Matrix Index.

When columns are inserted or updated within a table, the EMI engine is used to update any EMI associated with that table illustrated in the flowchart 250 in FIG. 12. If, for example, a column is inserted into the table, the EMI engine creates a variation vector, which includes one bit for every sub-column/sub-unit in the new column along with the offsets and lengths associated with the sub-units in the sub-unit data structure. Each bit of the variation vector is initialized to be off ("0"). The data for the first insert row may be stored as the reference data structure as disclosed above. The values for each row are compared to the reference data structure. If the values match ("Yes" branch of decision block 252), then processing continues for the next sub-unit (block 266). If there is a variation between the sub-unit value for any of the rows and the reference data structure ("No" branch of decision block 252), then the variation vector bit for the first sub-unit is checked. If the variation vector bit is off ("Yes" branch of decision block 254), then the bit of the variation vector corresponding to the sub-unit is changed to a "1", e.g. turned on (block 256). A value vector bitmap is created for the sub-unit (block 258) and mapped values for each of the previous rows are appended to the value vector using the map structure associated with the sub-column (block 260). A pointer is added to the sub-unit data structure to point to the newly created value vector (block 262). The mapped value of the current row is then appended to the value vector (block 264). If the variation vector bit is already on indicating a variation in the sub-unit ("No" branch of decision block 254), then the mapped value of the current row is then appended to the value vector (block 264). If there are additional sub-units ("Yes" branch of decision block 266), the process continues at block 252. If all sub-units have been processed ("No" branch of decision block 266), the process completes at block 268.

This same process may be used for a column that has been updated as well. The variation vector and sub-unit offsets and lengths may be updated in block 252. If the bit of the variation vector corresponding to the sub-unit is off ("Yes" branch of decision block 254), then the process continues at block 256 as disclosed above. However, if the variation vector bit is on ("No" branch of decision block 254), then a variation has already been indicated for the sub-unit and the mapped value for the row is appended and processing continues with a check for the next sub-unit at block 266.

While the embodiment discussed above in connection with FIGS. 1-7 described the use of an EMI in connection with telephone number data, it will be appreciated that EMIs can be used with innumerable other types of data. For example, as described above genomic sequence data is typically represented as long sequences of letters or numbers each having a small number of distinct values. As identified above, storing each single nucleotide polymorphism (SNP) or nucleotide as a separate column is generally not practical. Furthermore, it is inefficient to store the data as separate rows because users typically input and view the data as sequences of data. Therefore, storing each sequence in a single column with a row for each patient is appealing. The EMI disclosed above is well suited to leverage the characteristics of the data that each sub-unit of the sequence (e.g. the nucleotide or SNP) has a small number of unique values whereas the entire sequence is likely to have many variations that make each sequence unique. In other words, the EMI may leverage the fact that there are large portions of the sequence that are the same.

Figure 13:
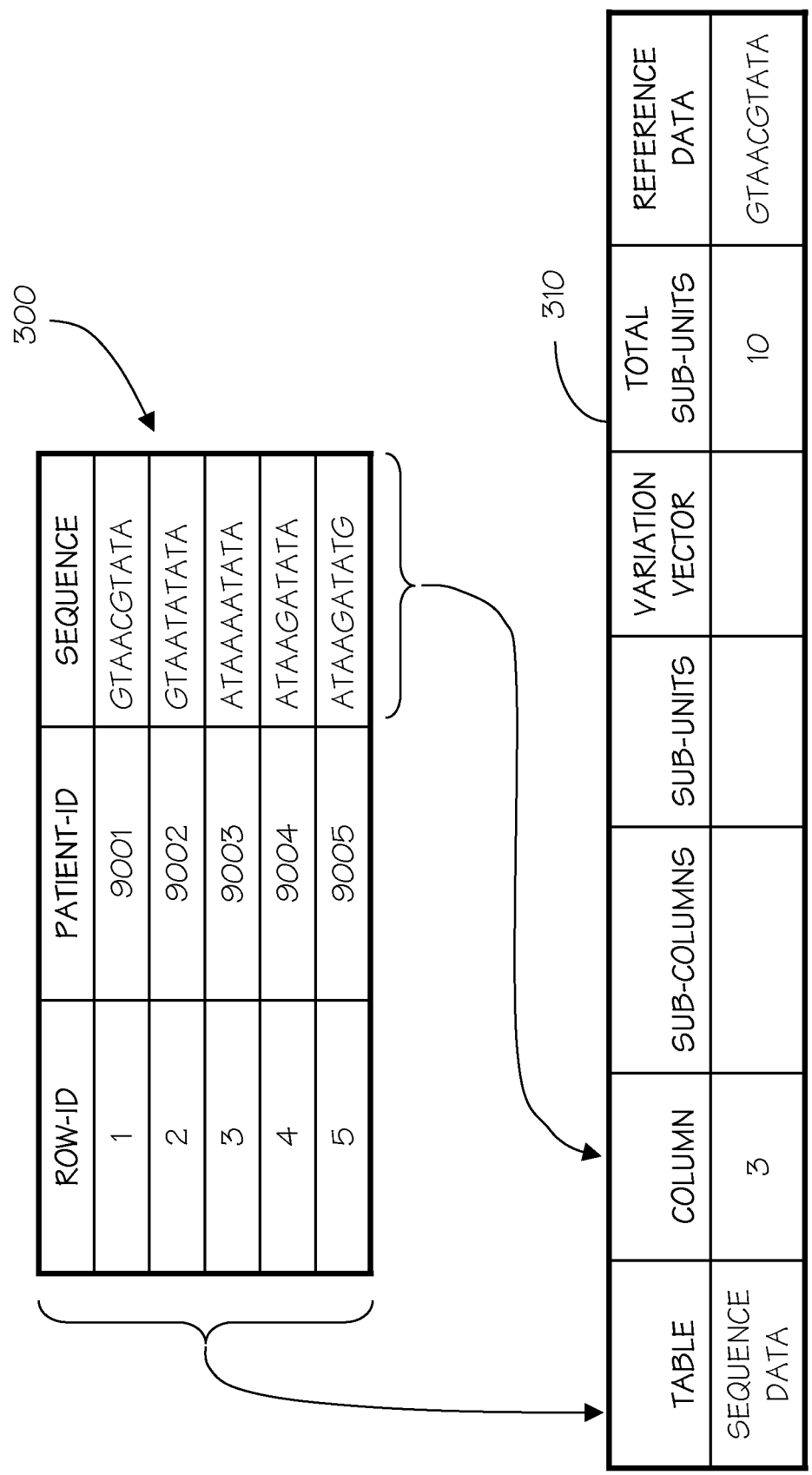
FIG. 13 shows an exemplary table containing genome sequence data and an associated Encoded Matrix Index control data structure.

Consider a small sample of patient data such as in table 300 in FIG. 13. Each row represents a sequence of nucleotides for a patient with a specified Patient ID. In this example, the sequence data would be defined to the EMI engine as a single sub-column named Nucleotide which is an array of one-character elements with possible values of A, G, T, or C. For example, an EMI control data structure 310 indicates that the EMI is being constructed for column 3 of the table 300 and that there will be a total of 10 sub-units corresponding to the sequences of 10 nucleotides. An exemplary SQL statement that could be used to define the EMI for the column may be:

CREATE ENCODED MATRIX INDEX ON SCHEMA.SEQDATA(SEQUENCE) WITH SUBCOLUMNS(NUCLEOTIDE ARRAY(10) OF CHAR (1)) CHECK(NUCLEOTIDE IN ('A', 'G', 'T', 'C'))

Given this, the EMI Engine would create a sub-column data structure 320 as shown in FIG. 13. The offset value for the sub-column is the offset of the start of sub-column data in bytes within the column, in this case the offset would be zero since there is only one sub-column. The length is the length of the sub-column in bytes, here 10, one byte for each character representing the nucleotide. Therefore the element length would be 1 byte. The Map Length for the map data structure is determined based on the number of possible values specified for the sub-column as disclosed above. In this example, because there are 4 possible values, the map may be 2 bits long. The sub-unit offset is the number of subunits that precede this sub-column within the column. Because this column only has one sub-column, the offset is 0.

The EMI engine also defines a mapping data structure of the possible values to a bitmap. In the present example, the EMI engine chose to map A=00, G=01, C=10, and T=11 as seen in the map data structure 322 in FIG. 14. The sub-unit data structure 330 may then be created as discussed above with the sub-unit data structure 330 containing ten entries, one for each of the elements in the array in the NUCLEOTIDE sub-column. Upon comparison of each of the sub-units to the reference data structure, a variation vector is created indicating a variation in the first, fifth, sixth, and tenth sub-units. Appropriate value vectors 332-338 are generated for each of the corresponding sub-units for which a variation exists. After the EMI has been generated, it can now be used with database queries to query the sequence data.

Figure 14:
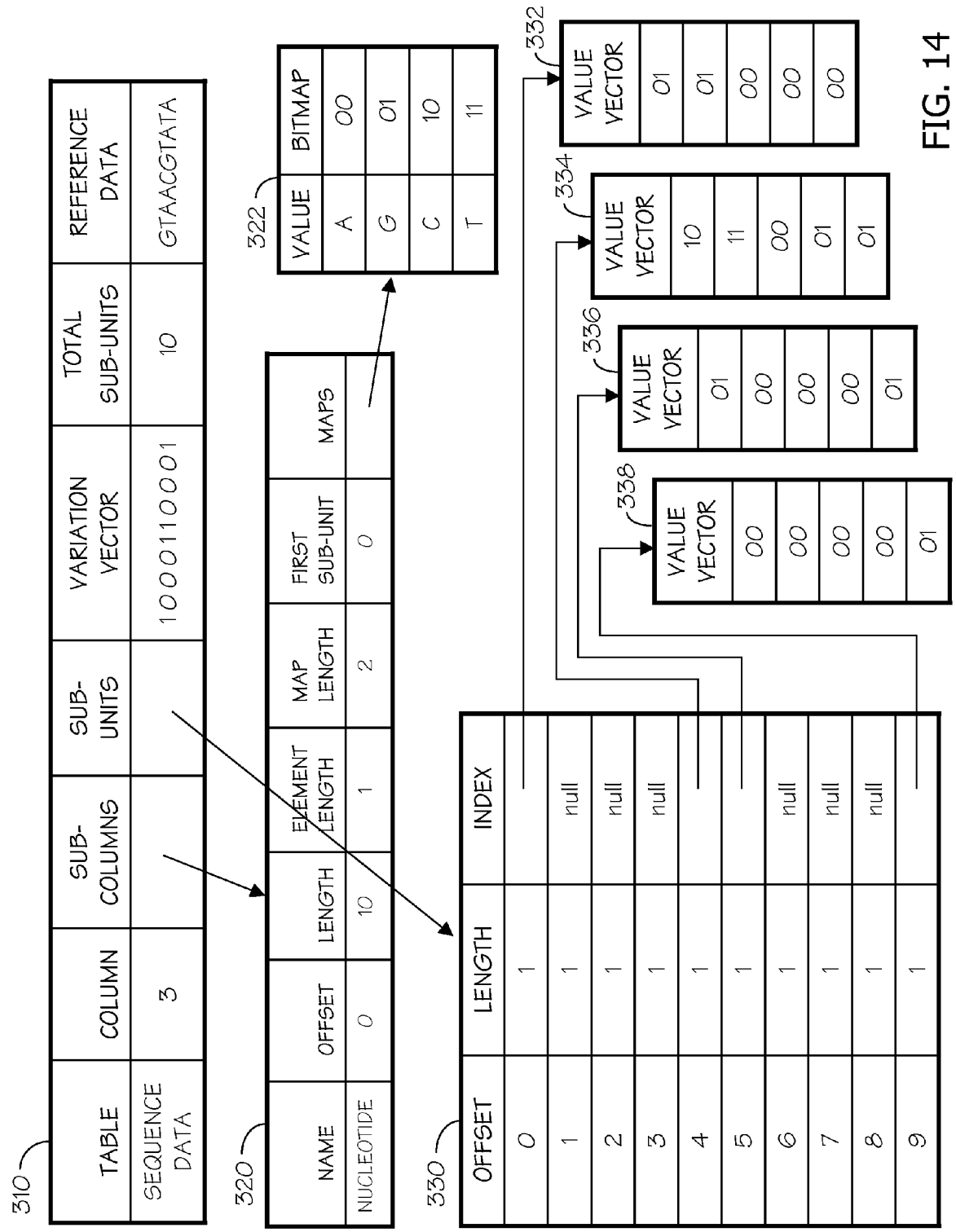
FIG. 14 shows the data structures associated with table and Encoded Matrix Index control data structure of FIG. 13.

A query may specify a sub-unit using a notation involving the column name, the sub-column name, and the element number when the sub-column is an array. For example, for a column named SEQUENCE and a sub-column array named NUCLEOTIDE, as illustrated in FIG. 13 and FIG. 14, the query may specify a name such as SEQUENCE.NUCLEOTIDE[1]. When a query specifies a condition involving a sub-column, the EMI engine may use the EMI control data structure 310 to navigate to the sub-column data structure 320. The EMI engine may then use the sub-column data structure 320 to determine the position of the sub-unit within the column, the sub-unit's corresponding bitmap length, and to navigate to the maps data structure 322 to find the bitmap representation of the value specified on the condition of the query. Using the sub-units position within the column, the EMI engine looks at the corresponding bit within the variation vector to determine if the sub-unit has variation across the rows of data. As disclosed above, if it does, the EMI engine uses the value vector to determine the value for each row. If not, the value is retrieved from the reference data structure.

For example, consider a query such as the following:

SELECT Patient_ID WHERE Sequence..Nucleotide
 [2]="A" AND Sequence..Nucleotide[4]="T"
 FROM Schema/SeqData The sequence column in table 300 has a sub-column named Nucleotide defined in the EMI structure in FIG. 13 and FIG. 14. The query values are mapped to bitmap representations using the map data structure 322 associated with the Nucleotide sub-column. For example, using the map data structure 322, the first predicate "A" is mapped to "00" and the second predicate "T" is mapped to "11". The element length in the sub-column data structure 320 is checked and is a "1" for both predicates, indicating that the sub-column Nucleotide is an array of values. For the first predicate, a pointer is set to an offset of 2, indicating the third sub-unit in the Nucleotide sub-column. The corresponding bit in the variation vector is a "0" indicating that there is no variation of the value based on the reference column across all of the rows of the table. For the first predicate, the value may be retrieved from the reference column at the third position, one character in length, resulting in a value of "A". The first part of the query related to the first predicate would result in all of the rows being selected. Next, for the second predicate, a pointer is set to an offset of 4, indicating the fifth sub-unit in the Nucleotide sub-column. The corresponding bit in the variation vector for the second predicate is a "1" indicating that there is a variation across the rows for this sub-unit. The value for this predicate is retrieved from a value vector 334 associated with the fifth sub-unit. The mapped predicate value "11" is now compared to the bitmap values for each of the rows in the value vector 334, with a match being found at row 2. Row 2 is returned and when ANDed with the results from the first predicate, selects the Patient_ID "9002" from row 2 of table 300.

Advantages of using an index, such as the Encoded Matrix Index include the following. Data can be stored within the most natural means, which is a single column per sequence. A maps data structure may be used to reduce the size of the index. A single column of data can be divided into sub-units for facilitating query construction. Portions of the column data that are common across rows are stored once rather than being duplicated throughout the index, enabling quick look-ups of these portions. Efficient vectors can be used for portions of the columns, which vary across rows to facilitate query operations.

EMIs may contain additional or fewer data structures than those presented in the embodiments above. For example, data in the sub-columns data structure and sub-unit data structure may be combined and implemented in a single data structure. Data may be mapped into forms other than bitmap values or actual value data may be stored in the value vector data structures, omitting the mapping steps and the need for map data structures. The variation data structure, which is implemented as a string of binary bits, may be incorporated directly into the sub-units data structure, eliminating the need for an additional data structure for variation. Alternatively, the variation data structure may be constructed using other means besides bit values to indicate variations in the rows of a sub-unit, such as a vector storing a number of variations rather than just an indication of a variation. The reference data structure may be populated as disclosed above by using the sequence data from the first row as a reference value. Alternatively, the reference value in the reference data structure may be selected from a predetermined target value. The reference value may also be constructed from different rows for different sub-units. Additionally the reference column data structure may contain multiple reference values in a vector form rather than a string that is parsed by an EMI engine. One of ordinary skill in the art would also recognize that the sub-columns defined within a column are not required to be distinct from one another, but could also overlap if it would be an appropriate way to sub-divide the sequence data in the column.

While the present invention has been illustrated by a description of one or more embodiments thereof and while these embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the scope of the general inventive concept.

What is claimed is:

1. A method of executing a database query using an Encoded Matrix Index, the method comprising, in response to a database query that includes a term associated with a sub-column defined in a column of a database table:
   accessing a variation data structure from the Encoded Matrix Index to determine whether any variation exists between rows belonging to the sub-column of the database table;
   in response to determining that no variation exists, accessing a value from a reference data structure from the Encoded Matrix Index that is associated with the sub-column and determining whether the value from the reference data structure matches the term in the database query; and
   in response to determining that a variation exists, accessing a value data structure from the Encoded Matrix Index that identifies a value for each row of the sub-column to determine which elements of the sub-column, if any, match the term in the database query.

2. The method of claim 1 wherein the value data structure includes a bitmap mapping of the value.

3. The method of claim 1 wherein the variation data structure is binary structure having a bit for each sub-column of the column, wherein each bit within the structure indicates a variation for a corresponding sub-element.

4. An apparatus comprising:
   a processor; and
   program code configured to be executed by the processor to execute a database query using an Encoded Matrix Index, the program code configured to, in response to a database query that includes a term associated with a sub-column defined in a column of a database table, access a variation data structure from the Encoded Matrix Index to determine whether any variation exists between rows belonging to the sub-column of the database table, in response to determining that no variation exists, access a value from a reference data structure from the Encoded Matrix Index that is associated with the sub-column and determine whether the value from the reference data structure matches the term in the data base query, and, in response to determining that a variation exists, access a value data structure from the Encoded Matrix Index that identifies a value for each row of the sub-column to determine which elements of the sub-column, if any, match the term in the database query.

5. The apparatus of claim 4 wherein the value data structure includes a bitmap mapping of the value.

6. The apparatus of claim 4 wherein the variation data structure is binary structure having a bit for each sub-column of the column, wherein each bit within the structure indicates a variation for a corresponding sub-column.

7. A program product, comprising:
   a non-transitory computer readable medium; and
   program code configured to execute a database query using an Encoded Matrix Index, the program code resident on the computer readable medium and configured to, in response to a database query that includes a term associated with a sub-column defined in a column of a database table, access a variation data structure from the Encoded Matrix Index to determine whether any variation exists between rows belonging to the sub-column of the database table, in response to determining that no variation exists, access a value from a reference data structure from the Encoded Matrix Index that is associated with the sub-column and determine whether the value from the reference data structure matches the term in the data base query, and, in response to determining that a variation exists, access a value data structure from the Encoded Matrix Index that identifies a value for each row of the sub-column to determine which elements of the sub-column, if any, match the term in the database query.

8. The program product of claim 7 wherein the value data structure includes a bitmap mapping of the value.

9. The program product of claim 7 wherein the variation data structure is binary structure having a bit for each sub-column of the column, wherein each bit within the structure indicates a variation for a corresponding sub-column.

10. The method of claim 1 wherein the Encoded Matrix Index includes a map structure that maps each distinct value of the sub-column to a bitmap representation, wherein the value data structure stores the bitmap representation of the value for each row, the method further comprising, in response to determining that the variation exists, accessing the map structure to identify a bitmap representation matching the term.

11. The method of claim 10 further comprising creating a dynamic bitmap by comparing the bitmap representation matching the term against the bitmap representation of the value for each row.

12. The apparatus of claim 4 wherein the Encoded Matrix Index includes a map structure that maps each distinct value of the sub-column to a bitmap representation, wherein the value data structure stores the bitmap representation of the value for each row, and wherein the program code is further configured to, in response to determining that the variation exists, access the map structure to identify a bitmap representation matching the term.

13. The apparatus of claim 12 wherein the program code is further configured to create a dynamic bitmap by comparing the bitmap representation matching the term against the bitmap representation of the value for each row.

14. The program product of claim 7 wherein the Encoded Matrix Index includes a map structure that maps each distinct value of the sub-column to a bitmap representation, wherein the value data structure stores the bitmap representation of the value for each row, and wherein the program code is further configured to, in response to determining that the variation exists, access the map structure to identify a bitmap representation matching the term.

15. The program product of claim 14 wherein the program code is further configured to create a dynamic bitmap by comparing the bitmap representation matching the term against the bitmap representation of the value for each row.

\* \* \* \* \*